(12) United States Patent
Reiner

(10) Patent No.: US 7,615,547 B2
(45) Date of Patent: Nov. 10, 2009

(54) GRANULATES CONTAINING LIPOSOLUBLE SUBSTANCES AND A PROCESS FOR THE PREPARATION THEREOF

(75) Inventor: Alberto Reiner, Como (IT)

(73) Assignees: APR Applied Pharma Research SA, Balerna (CH); Fidia Farmaceutici SpA, Padua (IT); Ipsen SpA, Milan (IT)

( * ) Notice: Subject to any disclaimer, the term of this patent is extended or adjusted under 35 U.S.C. 154(b) by 191 days.

(21) Appl. No.: 10/258,004

(22) PCT Filed: Jul. 9, 2002

(86) PCT No.: PCT/EP02/07636

§ 371 (c)(1),
(2), (4) Date: Oct. 15, 2002

(87) PCT Pub. No.: WO03/005989

PCT Pub. Date: Jan. 23, 2003

(65) Prior Publication Data

US 2004/0009232 A1    Jan. 15, 2004

(51) Int. Cl.
*A61K 31/56* (2006.01)
*A61K 9/16* (2006.01)
*A61K 9/08* (2006.01)
*A01N 43/00* (2006.01)

(52) U.S. Cl. ............... 514/178; 424/489; 424/499; 514/952

(58) Field of Classification Search ......... 424/464–465, 424/489, 499; 514/951–952, 960, 178
See application file for complete search history.

(56) References Cited

U.S. PATENT DOCUMENTS

| | | | | |
|---|---|---|---|---|
| 4,814,175 A | * | 3/1989 | Tack et al. | |
| 5,338,732 A | * | 8/1994 | Atzinger et al. | 514/178 |
| 5,527,543 A | * | 6/1996 | Dopper et al. | 424/489 |
| 5,976,570 A | * | 11/1999 | Greaves et al. | 424/470 |
| 5,985,309 A | * | 11/1999 | Edwards et al. | |
| 6,028,065 A | * | 2/2000 | Ragunathan et al. | |
| 6,224,909 B1 | * | 5/2001 | Opitz et al. | |
| 6,316,029 B1 | * | 11/2001 | Jain et al. | 424/484 |

FOREIGN PATENT DOCUMENTS

| | | |
|---|---|---|
| EP | 0 519 351 A2 | 12/1992 |
| EP | 0 914 822 A1 | 5/1999 |
| EP | 1008354 * | 6/2000 |
| JP | 04-049232 | 2/1992 |
| JP | 09-071529 | 3/1997 |
| WO | 94/21371 A1 | 9/1994 |
| WO | 95/09626 A1 | 4/1995 |
| WO | 00/30616 A1 | 6/2000 |

OTHER PUBLICATIONS

Howard C. Ansel, Introduction to Pharmaceutical Dosage, 4th edition, pp. 151 and 220.*
Ansel, Howard, Granules, 1993, Introduction to Pharmaceutical Dosage Forms, p. 123.*

* cited by examiner

Primary Examiner—Johann R Richter
Assistant Examiner—Andriae M Holt
(74) Attorney, Agent, or Firm—Mayer & Williams PC; Mark D. Wieczorek

(57) ABSTRACT

A process is described for the preparation of granulates that contain liposoluble and hydrophobic substances, preferably steroidal substances, and that exhibit rapid and excellent water-dispersibility. The process comprises:
  a) the dispersion of substance (A) in water in the presence of a surfactant (B),
  b) the incorporation of a water-soluble polyhydroxylated solid excipient (C) in the aqueous dispersion until a granulable pasty mass is obtained and
  c) the granulation of the mass.

Figure 1:
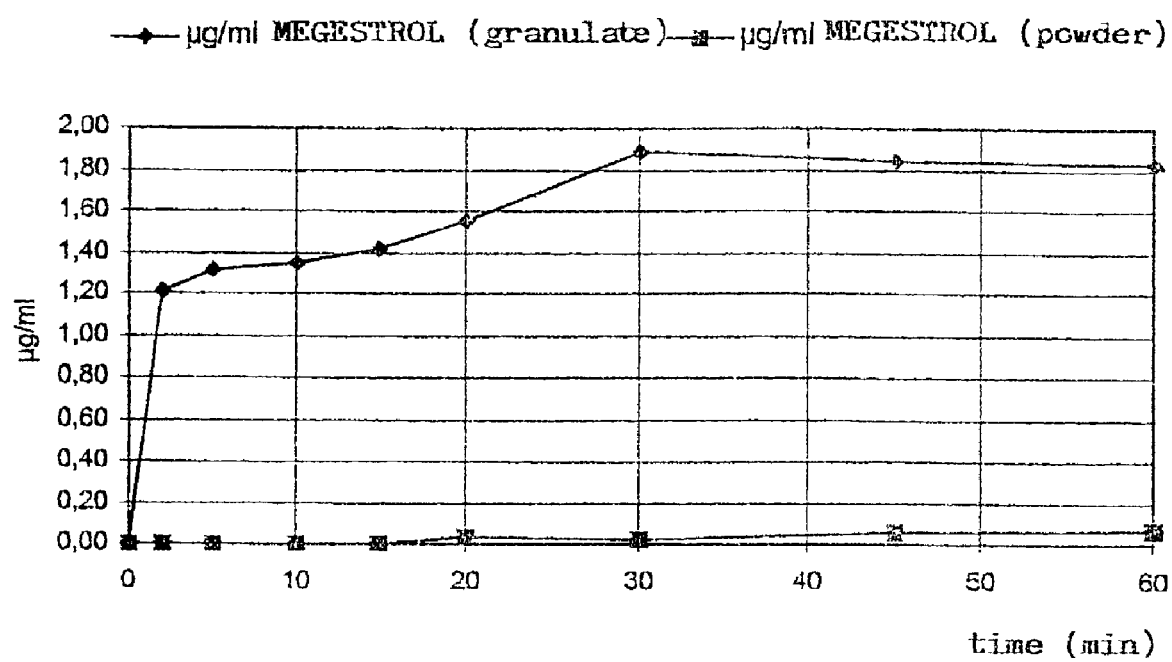

The granulates so obtained are suitable for the preparation, at the time of use, of stable and homogeneous aqueous suspensions that are used for nutritional, cosmetic or, preferably, pharmaceutical purposes.

16 Claims, 1 Drawing Sheet

GRANULATES CONTAINING LIPOSOLUBLE SUBSTANCES AND A PROCESS FOR THE PREPARATION THEREOF

This application is a national stage application for PCT/EP02/007636 filed under 35 U.S.C. 371, filed Jul. 9, 2002.

The present invention relates to a process for the preparation of granulates containing liposoluble substances and, more especially, relates to a process for preparing granulates that contain liposoluble substances and that exhibit immediate dispersibility in water and that are therefore suitable for the preparation, at the time of use, of stable and homogeneous aqueous suspensions that are used for nutritional, cosmetic or, preferably, pharmaceutical purposes.

TECHNICAL FIELD OF THE INVENTION

The poor water-solubility of some hydrophobic substances can make the preparation of their stable aqueous dispersions particularly problematic, regardless of whether this is in the field of nutrition, cosmetics or pharmaceuticals.

In the pharmaceutical sector in particular, the marked liposolubility of some classes of compound sometimes prevents the study and development of some formulations which could be produced in order to offer the drug to patients under improved conditions and with improved pharmacological properties, with great advantages in therapeutic practice. The improvement in the solubility of an active substance generally corresponds both to the achievement of higher blood levels in vivo, perhaps obtainable in even shorter times, and to a lower absorption variability, which occurs above all when the drug has poor bio-availability.

Using surface-active agents, which help to reduce the surface tension of particles, it is generally possible to disperse liposoluble substances in water to give relatively stable pseudo-solutions, suspensions or emulsions.

However, some classes of compound, for example, steroidal substances and, in particular, megestrol acetate, exhibit distinctive hydrophobic characteristics.

The above-mentioned megestrol acetate is a progestin which is widely used both in the field of contraceptives and as an anti-tumour agent and which is distributed by Bristol Myers Squibb under the mark Megace® (Merck Index, 1996, no. 5849). Megestrol acetate, like various other substances for therapeutic, cosmetic or nutritional use, is a hydrophobic compound which, in addition to exhibiting extremely poor water-solubility (2 µg/ml), is characterised by a high contact tension and is therefore difficult to wet.

Another disadvantage is the fact that the surface of the particles tends to absorb and trap air, thereby causing the product to float on the surface of the water.

Owing to those characteristics, the dispersion in aqueous medium of megestrol acetate and, more generally, substances having similar properties, constitutes a problem which is difficult to solve. In fact, it is usually impossible to obtain satisfactory and sufficiently stable dispersions in water either by the simple addition of surfactants or by micronisation: in the latter case, a deterioration in solubility is in fact observed, which is due to the fact that the micronisation of the compound greatly increases the surface area of the particles and, therefore, the enclosed air and the tendency to float.

All those disadvantages generally make it necessary to abandon the preparation of aqueous formulations of said substances, whereas, in various applications, it would be particularly advantageous to succeed in dispersing them adequately in water.

For example, in the pharmaceutical field it would be useful to be able to administer certain particularly hydrophobic substances, such as megestrol acetate, by the oral route, in the form of aqueous liquid formulations, especially in situations in which the patient has difficulty in swallowing solid forms or when the treatment provides for a high dosage which would require the ingestion of a large number of tablets or capsules.

For example, the treatment of cachexy, which is manifested by patients suffering from AIDS, is a typical form of therapy using a high dosage of megestrol acetate (EP338404).

Various formulation studies have been undertaken to improve the dissolvability in water of poorly water-soluble substances but, as far as we know, the only known examples of aqueous formulations for the oral administration of megestrol acetate are the syrups referred to in EP519351 and U.S. Pat. No. 6,028,065.

Those syrups are defined by the inventors as being "flocculated aqueous suspensions", prepared by dispersing in water a mixture of megestrol acetate, a surfactant such as polysorbate 80, and a hydrophilic polymer at concentrations of from 5% to 30%, such as polyethylene glycol, propylene glycol, glycerol or sorbitol.

However, the suspensions described above, in which the megestrol acetate is partly suspended and partly flocculated and in a layer at the bottom of the bottle, are definitely not the ideal form for correct oral administration because, even if they are suitably agitated, they do not ensure homogeneous distribution of the active substance and therefore reliable and repeatable dosage.

We have now surprisingly found that it is possible to granulate and then to disperse in water liposoluble substances that are not wettable and that float on water, such as megestrol acetate, in a complete, rapid and homogeneous manner and thus to prepare at the time of use stable aqueous formulations that are unquestionably useful in the field of nutrition, cosmetics and, in particular, pharmaceuticals.

The granulates of the present invention are particularly advantageous compared with the syrups of the prior art because they are stable over time, easy to handle and transport and are non-bulky. They also advantageously enable the compound to be dispersed in water at the moment of use, thus providing at the time of use homogeneous stable aqueous preparations with a precise and, if necessary, high dosage of the liposoluble substance.

DESCRIPTION OF THE INVENTION

The present invention therefore relates to a process for preparing granulates that exhibit rapid and excellent water-dispersibility and that contain liposoluble and hydrophobic substances, which process comprises:
  a) the dispersion of substance (A) in water in the presence of a surfactant (B),
  b) the incorporation of a water-soluble polyhydroxylated solid excipient (C) in the aqueous dispersion until a granulable pasty mass is obtained and
  c) the granulation of the mass.

The present invention permits the preparation of solid and stable granulates which, once placed in an aqueous medium, ensure not only that the liposoluble compound is immediately wetted but that it is diffused in an excellent manner in the water to provide a stable lactescent microsuspension.

The process of the invention relates to the granulation of liposoluble and hydrophobic substances (A), regardless of whether they are for nutritional, cosmetic or, preferably, pharmaceutical use.

In the present context, liposoluble substances are to be understood as meaning those substances, especially those active substances, which exhibit very poor water-solubility, preferably lower than 20 µg/ml, at 20° C. In addition, these substances are particularly hydrophobic, that is to say, practically non-wettable.

According to the present invention, the substances that can be formulated are generally any substances characterised by poor water-solubility and wettability, irrespective of whether they are used in the field of nutrition, cosmetics or pharmaceuticals.

In the pharmaceutical field, the classes of the steroids and, preferably, megestrol acetate, may be mentioned by way of non-limiting example.

The process to which the present invention relates comprises initially the dispersion of the water-insoluble substance in water in the presence of a surfactant (B).

The surfactants used are generally non-ionic surfactants, such as, for example, poloxamers, polyoxyethylene alkyl ethers, polyoxyethylene stearates, polyoxyethylene glycol hydroxy stearates and the fatty acid esters of polyoxyethylene sorbitans or polysorbates. A preferred group of non-ionic surfactants comprises the polysorbates, such as polysorbate 20, 40, 60, 65, 80 and 85, more preferably polysorbate 80 (Tween 80®).

In addition to ensuring that the water-insoluble substance is distributed uniformly in the selected soluble polyalcohols, those surfactants make it possible to obtain a finished granulate which is compact and heavy but which has the characteristic of dispersing the liposoluble substance uniformly as soon as the granulate is placed in water.

The dispersion of the liposoluble substance in water is generally carried out at a temperature of from 20° C. to 60° C., preferably from 25° C. to 40° C.

According to the present invention, the lipsoluble substance, preferably megestrol acetate, is dispersed in an excellent manner in the aqueous solvent in the presence of a surfactant, and then a water-soluble polyhydroxylated solid excipient (C) is added to it until a granulable pasty mass is obtained.

The excipient is generally a solid water-soluble polyhydroxylated compound selected from soluble polyalcohols, such as mannitol or sorbitol, and/or sugars, such as, for example, lactose or fructose, and mixtures thereof. In the present context, mannitol is particularly preferred.

The polyhydroxylated compounds (C) selected as solubilisers and dispersants of the water-insoluble substance, especially megestrol acetate, are used in an amount by weight, relative to the substance to be solubilised (A), of generally from 1:1 to 6:1 and, preferably, from 3:1 to 5:1, while the amount of selected surfactant (B) used, still calculated relative to the water-insoluble substance (A), ranges from 0.013:1 to 0.7:1, more advantageously from 0.02:1 to 0.33:1.

The process to which the present invention relates requires initially the dispersion of the water-insoluble substance in water in the presence of a surfactant.

The amount of water used is not a particularly important parameter because it can vary fairly freely, bearing in mind the necessity to ensure both good dispersion of the active substance and, subsequently, by gradual incorporation of the polyhydroxylated excipient, the production of a pasty mass which is neither too fluid nor excessively solid and which is suitable for granulation. Generally, the operation is carried out with quantities of water, expressed by weight relative to the water-insoluble substance (A), of from 0.2:1 to 1:1, preferably from 0.5:1 to 0.7:1.

The incorporation of the water-soluble polyhydroxylated solid excipient is generally carried out in portions and while agitating, in accordance with the method of successive dilutions, in order to confer the best possible dispersion and to obtain a pasty mass having the desired consistency.

Finally, the mass so prepared is subjected to granulation, preferably in a suitable mesh granulator.

The present invention relates also to the granulates obtainable using the above-described process and to the pharmaceutical forms that can be prepared using those granulates.

The granulates of the invention can be used as such or, preferably, can be utilised for the preparation, at the time of use, of oral aqueous dispersions characterised by stability and a precise posological content, or the granulates can be otherwise formulated.

These granulates for preparing, at the time of use, solutions for oral administration generally have a content of liposoluble substance, preferably megestrol acetate, in the final granulate of from 5 to 50% by weight, preferably from 15 to 25% by weight, and a particle size of from 5 to 180 µm, preferably from 30 to 160 µm. The aqueous dispersions according to the present invention prepared at the time of use are generally prepared by mixing the granulate with an amount of water equal to at least 80 ml per gram of granulate and by agitating until the granulate has completely dissolved.

These granulates are particularly suitable for the oral administration of even large amounts of liposoluble substances.

In the specific case of megestrol acetate, for example, it is possible to use the active substance in a single administration, in amounts of generally up to 320 mg, optionally even higher, and preferably approximately 160 mg.

The granulates of the invention can be formulated, optionally with the addition of other pharmaceutically acceptable excipients, such as, for example, effervescent mixtures, disintegrators, lubricants, sweeteners and flavourings, which improve the palatability of the suspensions or facilitate disintegration, in the form of packets, effervescent packets, syrups prepared at the time of use, tablets, effervescent tablets, quick-dissolving sublingual tablets.

For example, sweeteners, preferably synthetic sweeteners, such as saccharine, acesulfame, aspartame, cyclamate or mixtures thereof, are generally used in the oral formulations of the invention.

It is, however, important to emphasise that the above-mentioned additional excipients are not absolutely necessary to confer on the granulate the distinctive water-dispersibility which characterises it.

In a preferred embodiment of the present invention the predetermined amounts of water and polysorbate 80 are introduced into a suitable mixer and are agitated until the whole has been completely mixed and solubilised in the water at a temperature of from 25° C. to 40° C.

At that point, the megestrol acetate is added in portions, with agitation, to give a completely uniform suspension.

When the megestrol acetate has been completely suspended, the introduction of mannitol in small portions is initiated.

While still agitating slowly, the addition of mannitol is continued until a consistent finished mass capable of being granulated is obtained.

The mass is transferred to the granulator and is granulated on a mesh.

Finally, the granulate obtained is dried in an air bath.

The following Examples are now given for the purpose of better illustrating the present invention, but without limiting it.

EXAMPLE 1

Preparation of the Granulate

The standard procedure used for preparing the granulate based on megestrol acetate is sub-divided into the stages described hereinafter.

Stage I

Approximately 2.5 liters of water, and polysorbate 80 (100 g) were introduced into a suitable mixer provided with counter-rotating scraping blades and a turbine and having a capacity of 20 liters, and the whole was agitated until complete solubilisation in the water had occurred.

At that point 3 kg of megestrol acetate (Farmabios, particle size: $\leq$150 μm 88.21%; $\leq$36 μm 49.66%) were introduced in portions, with agitation, to give a completely uniform suspension. When the megestrol acetate had been completely suspended, introduction of the mannitol (4 kg, Carlo Erba) in small portions was initiated.

Agitation was continued until a homogeneous mixture was obtained which, however, had a density such that it could be readily transferred to a mixer of a size sufficient to contain the amount of mannitol which it was desired to add in order to obtain a suitable finished granulate.

Stage II

The mixture obtained in STAGE I was placed in the mixer provided. A further 13 kg of mannitol were added while agitating slowly. Agitation was continued for approximately 1 hour until a finished mass was obtained which was consistent and capable of being granulated.

Stage III

The mixture obtained in STAGE II was removed and was granulated on a 0.63 mm mesh or, alternatively, in a suitable granulator, for example with extrusion by rotating blades or a screw.

Stage IV

The granulate obtained was dried in an air bath.

The distribution of the megestrol acetate was checked (HPLC, standard method pharmacopoeia USP 24, ed. 2000, pages 1030-1032) and was found to be from 98.5% to 101.5%.

EXAMPLE 2

Preparation of an Aqueous Dispersion at the Time of Use

The granulate prepared according to Example 1 (900 mg) was placed in a beaker containing, water (100-150 ml) and agitated rapidly. An immediate and uniform dispersion of the granulate was observed, with the formation of a lactescent microsuspension suitable for oral use.

The dispersion so prepared demonstrates that the granulate of the invention is ideal for rapidly and homogeneously suspending liposoluble and hydrophobic substances in water. Unlike the syrups of the prior art, no separation or flocculation of the active substance is observed.

EXAMPLE 3

Dissolving Test

A comparative dissolving test was carried out between the granulate prepared according to Example 1 and the megestrol acetate powder (particle size: $\leq$150 μm 88.21%; $\leq$36 μm 49.66%)

The operating conditions were as follows:

| | |
|---|---|
| Medium: | water (900 ml) |
| Apparatus: | paddle |
| Rate of rotation of the blades: | 100 rpm |
| Temperature: | 37° C. |
| Reading wavelength: | 280 nm |

The following FIG. 1 shows that the granulate is characterised by optimum and rapid dispersibility in aqueous medium and is therefore particularly suitable for the preparation of aqueous formulations at the time of use.

Examples 4-7 given hereinafter illustrate the preparation, in accordance with conventional methods, of solid pharmaceutical forms that comprise the granulates of Example 1 and that are suitable for the oral administration of megestrol acetate.

EXAMPLE 4

Normal Packets

Each packet, having a total weight of 900 mg, has the following composition:

| | |
|---|---|
| Megestrol acetate: | 160.0 mg |
| Polysorbate 80: | 5.0 mg |
| Mannitol: | 640.0 mg |
| Aspartame: | 45.0 mg |
| Strawberry flavouring: | 50.0 mg |
| | (3.5% distillable essence supported on dextrose, maltodextrin, E414 gum arabic) |

EXAMPLE 5

Effervescent Packets

Each packet has the following composition:

| | |
|---|---|
| Megestrol acetate: | 160.0 mg |
| Polysorbate: | 5.0 mg |
| Mannitol: | 640.0 mg |
| Aspartame: | 40.0 mg |
| Citric acid: | 292.5 mg |
| Sodium bicarbonate: | 309.0 mg |
| Lemon flavouring: | 100.0 mg |

EXAMPLE 6

Effervescent Tablets

Each effervescent tablet has the following composition:

| | |
|---|---|
| Megestrol acetate: | 160.0 mg |
| Polysorbate 80: | 5.0 mg |
| Mannitol: | 640.0 mg |
| Aspartame: | 43.0 mg |
| Citric acid: | 390.0 mg |
| Sodium bicarbonate: | 412.0 mg |
| Lemon flavouring: | 100.0 mg |

EXAMPLE 7

Quick-Dissolving Sublingual Tablets

Each tablet has the following composition:

| | |
|---|---|
| Megestrol acetate: | 160.0 mg |
| Mannitol: | 390.0 mg |
| Aspartame: | 45.0 mg |
| Strawberry flavouring | 50.0 mg |
| Polysorbate 80: | 5.0 mg |

The invention claimed is:

1. A process for preparing a liquid suspension which is stable at the time of use, which process comprises:
   a) dispersing a liposoluble and hydrophobic substance having a water-solubility at 20° C. of less than 20 µg/ml in a medium consisting of water and a surfactant to create an aqueous dispersion, wherein the liposoluble and hydrophobic substance is a steroidal substance and wherein the dispersion is effected at a temperature of from 20° C. to 60° C.;
   b) incorporating a water-soluble polyhydroxylated solid excipient in the aqueous dispersion and therein obtaining a granulable pasty mass;
   c) granulating the pasty mass; and
   d) placing the thus-obtained granulate in an aqueous medium;
      wherein the amount of surfactant, by weight, relative to the amount of liposoluble and hydrophobic substance, is from 0.013 to 0.7;
      wherein the amount of water, by weight, relative to the amount of liposoluble and hydrophobic substance, is from 0.2 to 1; and
      wherein the amount of polyhydroxylated solid excipient, by weight, relative to the amount of liposoluble and hydrophobic substance, is from 1 to 6.

2. A process according to claim 1, wherein the liposoluble and hydrophobic substance is megestrol acetate.

3. A process according to claim 1, wherein the surfactant is a polysorbate.

4. A process according to claim 3, wherein the surfactant is polysorbate 80.

5. A process according to claim 1, wherein the dispersion of the liposoluble and hydrophobic substance in water is effected at a temperature of from 25° C. to 40° C.

6. A process according to claim 1, wherein the water-soluble polyhydroxylated solid excipient is selected from the group consisting of: mannitol, sorbitol, lactose, fructose and mixtures thereof.

7. A process according to claim 1,
   wherein the amount of surfactant, by weight, relative to the amount of liposoluble and hydrophobic substance, is from 0.02 to 0.33; and
   wherein the amount of polyhydroxylated solid excipient, by weight, relative to the amount of liposoluble and hydrophobic substance, is from 3 to 5.

8. A process according to claim 1, wherein the amount of water, by weight, relative to liposoluble and hydrophobic substance, is from 0.5 to 0.7.

9. A liquid suspension which is stable at the time of use which is produced by the process according to claim 1.

10. A process for preparing a liquid suspension which is stable at the time of use, the process comprising the steps of:
    a) dispersing a liposoluble and hydrophobic substance having a water-solubility at 20° C. of less than 20 µg/ml in a medium consisting of water and a polysorbate to create an aqueous dispersion, wherein the liposoluble and hydrophobic substance is a steroidal substance and wherein the dispersion is effected at a temperature of from 20° C. to 60° C.;
    b) incorporating a water-soluble polyhydroxylated solid excipient in the aqueous dispersion and therein obtaining a granulable pasty mass, wherein the water-soluble polyhydroxylated solid excipient is selected from the group consisting of: mannitol, sorbitol, lactose, fructose and mixtures thereof;
    c) granulating the pasty mass; and
    d) placing the thus-obtained granulate in an aqueous medium;
       wherein the amount of surfactant, by weight, relative to the amount of liposoluble and hydrophobic substance, is from 0.013 to 0.7;
       wherein the amount of water, by weight, relative to the amount of liposoluble and hydrophobic substance, is from 0.2 to 1; and
       wherein the amount of polyhydroxylated solid excipient, by weight, relative to the amount of liposoluble and hydrophobic substance, is from 1 to 6.

11. A process according to claim 10, wherein the liposoluble and hydrophobic substance is megestrol acetate.

12. A process according to claim 10, wherein the polysorbate is polysorbate 80.

13. A process according to claim 10, wherein the dispersion of the liposoluble and hydrophobic substance in water is effected at a temperature of from 25° C. to 40° C.

14. A process according to claim 10,
    wherein the amount of surfactant, by weight, relative to the amount of liposoluble and hydrophobic substance, is from 0.02 to 0.33; and
    wherein the amount of polyhydroxylated solid excipient, by weight, relative to the amount of liposoluble and hydrophobic substance, is from 3 to 5.

15. A process according to claim 10 wherein the amount of water, by weight, relative to liposoluble and hydrophobic substance, is from 0.5 to 0.7.

16. A liquid suspension which is stable at the time of use which is produced by process the process according to claim 10.

* * * * *